United States Patent [19]

Malinow

[11] Patent Number: 5,502,038
[45] Date of Patent: Mar. 26, 1996

[54] CHOLESTEROL SEQUESTRANT GLYCOSIDES THAT INHIBIT INTESTINAL CHOLESTEROL ABSORPTION

[75] Inventor: M. Rene Malinow, Portland, Oreg.

[73] Assignee: Medical Research Foundation of Oregon, Beaverton, Oreg.

[21] Appl. No.: 80,282

[22] Filed: Jun. 21, 1993

[51] Int. Cl.$^6$ ............... A61K 31/705; A61K 31/715; A01N 45/00; A01N 43/04
[52] U.S. Cl. ............... 514/26; 514/53; 514/54; 536/5; 536/6; 536/123.1; 536/123.13
[58] Field of Search ............... 514/26, 53, 54; 536/4.1, 6, 6.1, 5, 123.1, 123.13

[56] References Cited

U.S. PATENT DOCUMENTS

| | | | |
|---|---|---|---|
| 3,160,626 | 12/1964 | Oxley | 260/239.55 |
| 3,303,187 | 2/1977 | Rubin | 260/239.55 |
| 4,242,502 | 12/1980 | Malinow et al. | 536/5 |
| 4,260,603 | 4/1981 | Pegel et al. | 424/182 |
| 4,265,886 | 5/1981 | Pegel | 424/182 |
| 4,602,003 | 7/1986 | Malinow | 514/26 |
| 4,602,005 | 7/1986 | Malinow | 514/26 |
| 4,921,838 | 5/1990 | Catsimpoolas et al. | 514/25 |
| 4,929,603 | 5/1990 | Pegel et al. | 514/26 |
| 5,010,185 | 4/1991 | Urban | 536/6.1 |
| 5,017,562 | 5/1991 | Holmes et al. | 514/26 |

FOREIGN PATENT DOCUMENTS

| | | |
|---|---|---|
| 0403150 | 12/1990 | European Pat. Off. |
| 2425859 | 12/1979 | France |
| 9307167 | 9/1992 | WIPO |
| 9311150 | 10/1993 | WIPO |
| WO94/00480 | 1/1994 | WIPO |

OTHER PUBLICATIONS

McCarthy, Peter. *J. Labelled Comp.* vol. 28(10), pp. 1149–1159, (1990).
Ryff, I. M *Byull. Eksp. Biol. Med.*, vol. 106(9), pp. 365–368, (1988). (Abstract only).
Varvashtyan et al. Deposited Document w/Viniti, pp. 3763–3775 (8 pages), (1975) (Abstract only).
Kintya et al. *Khim.–Farm ZH.*, vol. 15(9), pp. 55–60, (1981).
Dimoglo et al., *Bioorganicheskaya Khimiya*, vol. 11, pp. 408–413, (1985).
Freire et al., *Chromatography in Biochemistry, Medicine and Environmental Research*, vol. 1, pp. 249–259, (1983).
Shchelochkova et al., "Diosgenin and Neotigogenin Glucosides," *Khimiya Priorodnykh Soedinenii*, 1:103–04 (1979).
*Chemical Abstracts*, vol. 91, 1979, p. 624, Abstract No. 74842b, Shchelochkova et al., "Glucosides of Diosgenin and Neotigogenin."
Morris et al., "Isolation, Purification, and Structural Identity of an Alfalfa Root Saponin," *J. Org. Chem.*, 26:1241–1243 (1961).
Segal et al., "Hemolytic Properties of Synthetic Glycosides," *J. Pharm. Sci.*, 67:1589–1592 (1978).
Sato et al., "A Bitter Principle of Tomato Seeds," *Agr. Biol. Chem.*, 37:225–231 (1973).
Malinow et al., "Prevention of Hypercholesterolemia in Monkeys (*Macaca fascicularis*) by Digitonin," *Am. J. Clin. Nut.* 31:814–818 (1978).
Malinow, "Effects of Synthetic Glycosides on Cholesterol Absorption," *Annals of the New York Academy of Sciences* 54:23–27 (1985).
Nes et al., "Isopentenoids in Plants Biochemistry and Function," Western Regional Research Center, Agricultural Research Service, Berkeley, California. p. 457 (1984).
Fruton et al., "Chemistry and Metabolism of Steroids," *General Biochemistry* (2nd ed.), John Wiley & Sons, Inc., New York, pp. 620–621 (19 ).
Heftmann et al., "Structure of Sapogenins," *Biochemistry of Steroids*, Reinhold Publishing Corporation, New York, p. 47 (1960).
Kintya et al., "Search for Hypocholesteremic Agents Among a Group of Steroid Glycosides," *Kim.—Farm, Zh.* 15:9, pp. 56–60 (1980?) (Russian–English translation included).
Perepelitsa et al., "A Chemical Study of the Steroid Glycosides of *Tribulus Terrestris*–IV. Steroid Saponins," *Khimya Prirodnykh Soedinenii* 2:260–261 (1975).
Lazur'evskii et al., "Structure of Steroid Glycosides of Leaves of *Funkia Ovata* Spr.," *Doklady Akademii Nauk SSSR* 230:476–477 (1976).
Lazur'evskii et al., "Steroid Glycosides from Leaves of *Agava americana* L., " *Doklady Akademii Nauk SSSR* 224:1442–1444 (1975).
Kintya et al., "Rockogenin Glycosides," *Khimiya Prirodnykh Soedinenii* 1:102–103 (1979).
*Chemical Abstracts*, 96:97470w (1982).
Malinow et al., "Effect of Alfalfa Saponins in Intestinal Cholesterol Absorption in Rats," *Am. J. Clin. Nutr.* 30:2061–2067 (1977).
Malinow et al., "Cholesterol and Bile Acid Balance in *Macaca fascicularis*," *J. Clin. Invest.* 67:156–162 (1981).
*The Merck Index*, pp. 439 and 1217 (1976).
Fieser et al., *Steroids*, p. 28 (1959).
Lazur'evskii et al., "Steroid Glycosides from *Asparagus Officinalis* L.," *Doklady ANSSR* (Reports of the USSR Academy of Sciences, 231:1479–1481 (1976).
Malinow et al., "Effects of Synthetic Glycosides on Steroid Balance in *Macaca fascicularis*," *J. Lipid Res.* 28:1–9 (1987).
Malinow et al., "Synthesis and Biological Activity of α– and β– Tigogenin Cellobiosides," *Steroids* 48:197–211 (1986).
Malinow et al., "Effects of Synthetic Glycosides on Cholesterol Homeostasis," *Circulation* 72:III–94 (1985).

Primary Examiner—Douglas W. Robinson
Assistant Examiner—Howard C. Lee
Attorney, Agent, or Firm—Klarquist Sparkman Campbell Leigh & Whinston

[57] ABSTRACT

Glycosides having neotigogenin aglycone moieties, administered orally to mammals are shown to inhibit the absorption of cholesterol. These compounds are useful in the treatment of hypercholesterolemia. Particular compounds are derived from tomato seeds and include neotigogenin trisaccharide.

4 Claims, No Drawings

CHOLESTEROL SEQUESTRANT GLYCOSIDES THAT INHIBIT INTESTINAL CHOLESTEROL ABSORPTION

FIELD OF THE INVENTION

The invention relates to compounds which, when administered orally to warm-blooded animals, inhibit the absorption of cholesterol.

BACKGROUND OF THE INVENTION

Certain water/alcohol soluble extracts from plant sources have been found to reduce cholesterolemia in chicks, pigs and rats (P. Griminger, et al., "Dietary Saponin and Plasma Cholesterol in the Chick." *Proc. Soc. Exp. Biol. Med.* 99:424–426, 1958; H. A. I. Newman, et al. "Dietary Saponins, a Factor Which May Reduce Liver and Serum Cholesterol Levels." *Poultry Sci.* 37:42–46, 1958; B. Morgan, et al., "The Interactions Between Dietary Saponin, Cholesterol and Related Sterols in the Chick." *Poultry Sci.* 51:677–682, 1972; D. L. Topping, et al., "Effects of Dietary Saponins in Fecal Bile Acids and Neutral Sterols, Plasma Lipids and Lipoprotein Turnover in the Pig." *Am. J. Clin. Nutr.* 33:783–786, 1980; D. G. Oakenfull, et al., "Effects of Saponins on Bile-acids and Plasma Lipids in the Rat." *Br. J. Nutr.* 42209–216, 1979; and D. L. Topping, et al., "Prevention of Dietary Hypercholesterolemia in the Rat by Soy Flour High and Low in Saponins." *Nutr. Rep. Int.* 22:513–519, 1980.)

Among these plant extracts, extracts from alfalfa hay have been shown to be active in reducing the absorption of dietary cholesterol. In particular, these alfalfa extracts reduce the intestinal absorption of cholesterol in rats and monkeys (M. R. Malinow, et al., "Cholesterol and Bile Acid Balance in Macaca fascicularis: Effects of Alfalfa Saponins," *J. Clin. Invest.* 67:156–162, 1981.) These alfalfa extracts have been shown to contain saponins identifiable by thin-layer chromatography. The alfalfa extracts contain, in addition to saponins, unspecified amounts of carbohydrates, amino acids, peptides, pigments, and free aglycones that are removed from alfalfa hay by the water solvent used during their preparation. The capacity of such alfalfa extracts to interfere with cholesterol absorption is enhanced by partial acid hydrolysis as reported in M. R. Malinow, et al., "Effect of Alfalfa Saponins on Intestinal Cholesterol Absorption in Rats," *Am. J. Clin. Nutr.* 30:2061–2067, 1977; and U.S. Pat. No. 4,242,502 (Malinow, et al.) herein incorporated by reference.

It was previously reported that the toxicity of plant saponins is decreased in rats, mice, and birds of by cholesterol in the diet (J. O. Anderson, "Effect of Alfalfa Saponin on the Performance of Chicks and Laying Hens." *Poult. Sci.* 36:873–876, 1957; I. Ishaaya, et al., "Soybean Saponins. IX. Studies of Their Effects on Birds, Mammals and Cold-blooded Organisms." *J. Sci. Food Agric.* 20:433–436, 1969; G. Reshef, et al., "Effect of Alfalfa Saponins on the Growth and Some Aspects of Lipid Metabolism of Mice and Quails." *J. Sci. Food Agric.* 27:63–72, 1976; E.G. Wilcox, et al., "Serum and Liver Cholesterol, Total Lipids and Lipid Phosphorus Levels of Rats Under Various Dietary Regimes." *Am. J. Clin. Nutr.* 9:236–243, 1961.

Despite these encouraging results, it remained a problem that plant extracts, which are of variable composition, contain a volume of nonuseful chemical substances. It is difficult, due to the variations in composition, to set a standard dosage or predict the impurities present. Thus, such extracts are not well suited for use by humans.

Subsequently, and as set forth in U.S. Pat. No. 4,602,003 (Malinow) and U.S. Pat. No. 4,602,005 (Malinow), which are herein incorporated by reference, it was discovered that certain synthetically produced, pure "sapogenin-derived" compounds, e.g., substances compounded from spirostane, spirostene, or sterol-derived compounds, are nontoxic. Specifically, U.S. Pat. Nos. 4,602,003 and 4,602,005 disclose the use of glycosides having a tigogenin or diosgenin aglycone moiety, such as tigogenin cellobioside, for the treatment of hypercholesterolemia and atherosclerosis. Such compounds were shown to depress cholesterol absorption more effectively than alfalfa extracts on a weight basis and thus can be administered in reasonably sized doses. Because the chemical compositions of these substances are known and because they can be synthesized at a high degree of purity, they can be used to treat any warm-blooded animal, including humans. However, the synthesis of these compounds, as set forth in U.S. Pat. No. 4,602,003, is complex, expensive and requires the use of large quantities of environmentally hazardous organic solvents such as chloroform, acetic acid and methanol and heavy metals such as silver or mercury.

Moreover, currently the only known commercially available source of the starting compound, tigogenin, is the plant *Agave sisalane*. This plant is grown commercially only in mainland China and Mexico and takes seven years to grow to maturity. Diosgenin can be obtained from several dioscoracaeae plants that are grown in Mexico.

SUMMARY OF THE INVENTION

The present inventions concerns the discovery that certain glycosides isolated from tomato seeds, and glycosides that are derived from these glycosides, are effective in reducing cholesterol uptake in the gastrointestinal tract of mammals. These glycosides have neotigogenin aglycone moieties and therefore differ from known glycosides having tigogenin aglycone moieties.

One compound encompassed by the present invention is neotigogenin trisaccharide. This compound is shown to be readily derived from a neotigogenin-based glycoside that is readily isolated from tomato seeds. Thus, neotigogenin trisaccharide can be economically produced in large quantities by a simple process from readily available starting materials. Neotigogenin trisaccharide is also shown to be more effective in reducing cholesterol uptake in mammals than the known tigogenin-based compounds such as tigogenin cellobioside.

Another aspect of this invention is the use of neotigogenin-based glycosides, such as neotigogenin trisaccharide, in a method of reducing cholesterol uptake in the gastrointestinal tract of a mammal. This method comprises administering to a mammal a therapeutically effective amount of compound comprising a glycoside having a neotigogenin aglycone moiety.

Neotigogenin trisaccharide can also be used in a method of treating hypercholesterolemia and atherosclerosis in a mammal. This method comprises administering to a mammal in need of such treatment a therapeutically effective amount of neotigogenin trisaccharide.

Also encompassed by the present invention is a pharmaceutical composition useful for treatment of hypercholesterolemia and atherosclerosis in mammals which comprises a pharmaceutically effective amount of a glycoside having a neotigogenin aglycone in admixture with a pharmaceutically acceptable excipient.

Additionally, compounds which are derivatives of the neotigogenin-based glycosides of the present invention and which may be used in the disclosed methods of treatment are also encompassed by the present invention.

DETAILED DESCRIPTION OF THE INVENTION

Definitions

As used hereinafter: "Tigogenin" means a compound of 5α,20α,22α,25D-spirostan-3β-ol, represented by the formula:

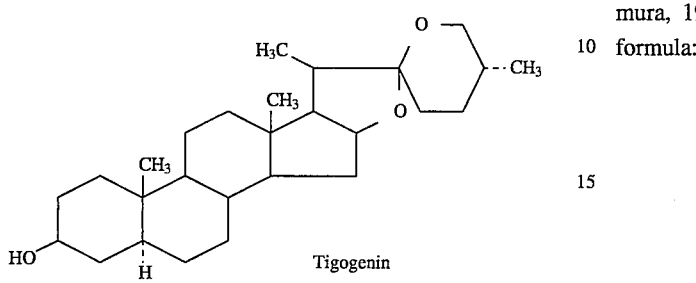

Tigogenin

"Neotigogenin" means a compound of 5α,20α,22α,25S-spirostan-3β-ol, represented by the formula:

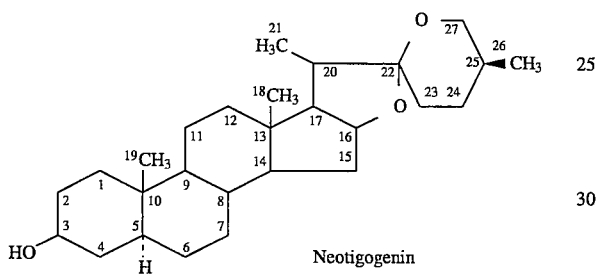

Neotigogenin

Numbering of the carbon molecules in this structure is as set forth for steroid sapogenin in Heftmann and Mosettig, *Biochemistry of Steroids*, Rheinhold publishing Corp., 1960. The difference between tigogenin and neotigogenin lies in the spatial configuration of the 25 $CH_3$ in these two molecules. The 25 $CH_3$ is in the axial (L or β) configuration in neotigogenin and in the equatorial (D or α) configuration in tigogenin.

"Tigogenin cellobioside" (also "tigogenyl cellobioside") means a non-separated mixture of α and β-anomers of tigogenin cellobioside and an individual α- and β-anomer of this compound, as set forth in U.S. Pat. Nos. 4,602,003 and 4,602,005. The β-anomer, represented by the formula shown below, is also known as "tiqueside".

"Neotigogenin trisaccharide" (also "Neotigogenyl trisaccharide") means a compound derived from furostane tetrasaccharide by the method set forth below in "Preparation Procedures". This compound has a proposed structure of: 5α-25β-spirostan-3-0-β-D-glucopyranosyl (1→2)-β-D-glucopyranosyl (1→4)-β-D-galactopyranoside (Sato and Sakamura, 1973). This proposed structure is depicted by the formula:

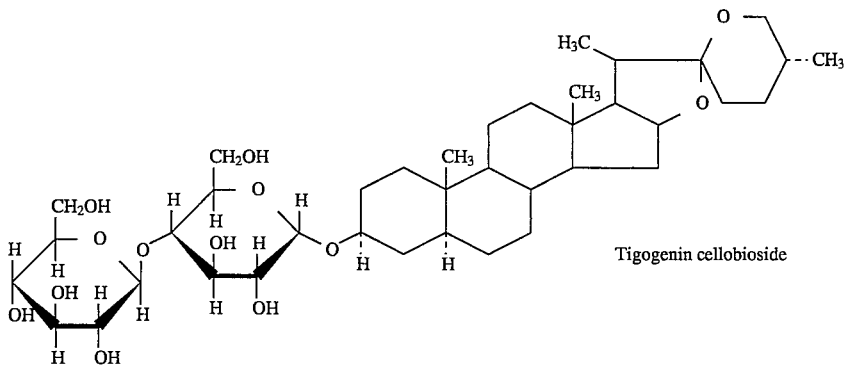

Tigogenin cellobioside

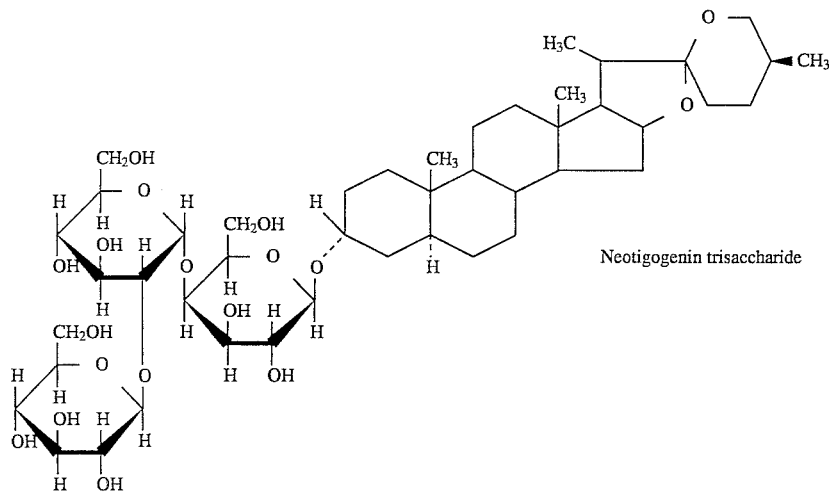

Neotigogenin trisaccharide

The proposed structure of neotigogenin trisaccharide can also be represented by the formula:

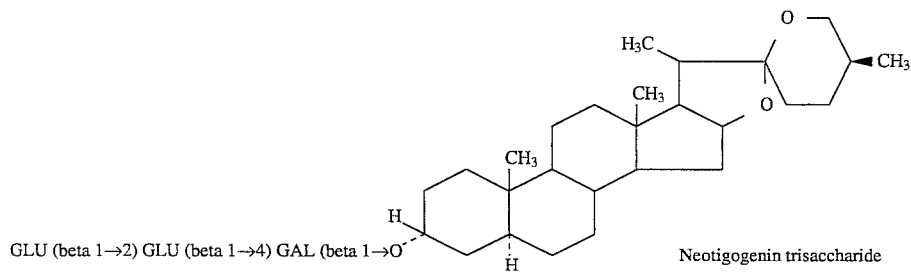

GLU (beta 1→2) GLU (beta 1→4) GAL (beta 1→O⁻)  Neotigogenin trisaccharide

"Furostane tetrasaccharide" means a compound of 5α-furostane-3$_\beta$, 22, 26 triol-3-[0-β-D-glucopyronosyl (1→2) -β-D-glucopyronosyl (1→4) -β-D-galactoyranoside]26-0-β-Dglucopyranoside (Sato and Sakamura, 1973). It is represented by the formula:

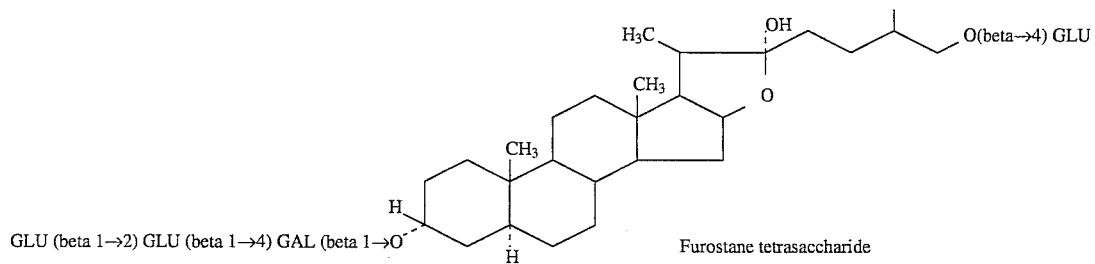

GLU (beta 1→2) GLU (beta 1→4) GAL (beta 1→O⁻)  Furostane tetrasaccharide

"Furostene tetrasaccharide" means a compound of 5 α-furost-20:22 ene-3β, 26 diol-3-[0-β-D-glucopyranosyl (1→2) -β-D-glucopyranosyl (1→4) -β-D-galactopyranoside] 26-0-β-D-glucopyranoside (Sato and Sakamura, 1973). It is

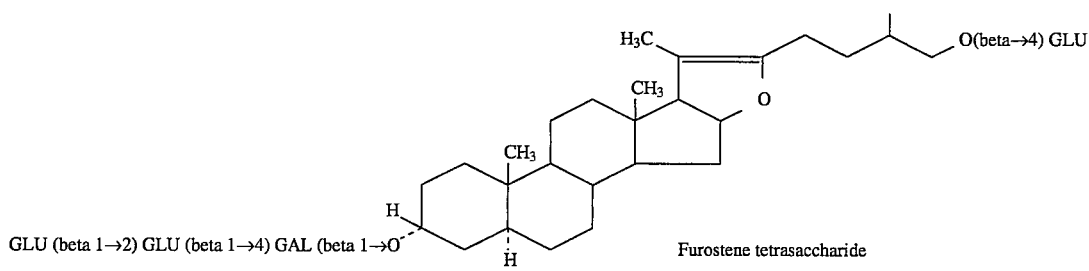

Furostene tetrasaccharide

"Glycoside" means an organic compound which can be resolved by hydrolysis into sugars and other organic substances known as "aglycones". Specifically, glycosides are acetals which are derived from a combination of various hydroxy compounds with various sugars.

"Aglycone" means a nonsugar hydrolytic product of a glycoside. Specifically, in the present invention, "neotigogenin aglycone" encompasses aglycone moieties comprising neotigogenin, furostene and furostane and therapeutically-effective derivatives of these compound wherein the C-25 is the α enantiomer.

"Mammals" means a class of warm-blooded vertebrates characterized by mammary glands, including but not limited to humans, laboratory or domestic animals such as dogs, cats, mice, rats or rabbits, and livestock.

"Treatment" covers any treatment of the disease in a mammal, particularly human, and includes:

(i) preventing the disease from occurring in a subject which may be predisposed to the disease but has not yet been diagnosed as having it;

(ii) inhibiting the disease, i.e. arresting the development of said disease; or (iii) relieving the disease, i.e. causing regression of the disease.

"Hypercholesterolemia" also known as hypercholesteremia or hypercholesterinemia, means the presence of an abnormally large amount of cholesterol in the cells and plasma of the circulating blood.

"Arteriosclerosis" as used herein means a degenerative arterial sclerosis marked by hardening and thickening of the vessel walls.

The types of arteriosclerosis generally recognized are atherosclerosis, Mönckeberg's arteriosclerosis, hypertensive arteriosclerosis, arteriolosclerosis or senile arteriosclerosis.

"Atherosclerosis" as used herein means:

(i) deposition of lipid with proliferation of fibrous connective tissue cells in the inner walls of arteries;

(ii) modular sclerosis; arteriosclerosis characterized by irregularly distributed lipid deposits in the intima of large and medium-sized arteries. Such deposits are associated with fibrosis and calcification, and are almost always present in some degree in the middle-aged and elderly.

"Hypertensive arteriosclerosis" means progressive increase in muscle and elastic tissue of arterial walls resulting from hypertension. In longstanding hypertension elastic tissue forms numerous concentric layers in the intima and there is replacement of muscle collagen fibers and hyaline thickening of the intima of arterioles. Such changes can develop with increasing age even in the absence of hypertension and may then be referred to as senile arteriosclerosis.

"Mönckeberg's arteriosclerosis" means (i) degeneration, (ii) sclerosis, or (iii) calcification.

Mönckeberg's arteriosclerosis generally means arterial sclerosis involving the peripheral arteries, especially of the legs of older people, with deposition of calcium in the medial coat (pipe-stem arteries) but with little or no encroachment on the vessel lumen.

"Arteriolosclerosis" means arteriolar sclerosis. Arteriolosclerosis affects mainly the small vessels called arterioles. Arteriolosclerosis can be seen especially in patients with chronic hypertension.

Preferred Embodiments

The present invention concerns glycoside compounds with a neotigogenin aglycone moiety. It has been found that these compounds are able to reduce the absorption of dietary cholesterol in mammals. Thus, these compounds will be of use in the treatment of hypercholesterolemia and atherosclerosis. The compounds of the present invention, namely glycosides having neotigogenin aglycone moieties are shown to be more effective in reducing cholesterol absorption than glycosides having tigogenin aglycone moieties.

In preferred embodiments of the present invention, the glycosides having neotigogenin aglycone moieties are isolated from tomato seeds or are derived from precursor compounds isolated from tomato seeds. The compounds include, in one embodiment, furostane tetrasaccharide and furostene tetrasaccharide. In a more preferred embodiment, the compounds of the present invention include neotigogenin trisaccharide. Methods of isolating these compounds from tomato seeds or synthesizing these compounds based on precursors isolated from tomato seeds are also disclosed herein.

Compounds of the present invention, including tomato seed glycosides and derivatives of these glycosides according to the invention, such as glycosides having a neotigogenin aglycone, successfully bind cholesterol and inhibit its absorption by the digestive system of warm-blooded animals. Thus far, no toxic effect has been associated with such substances. And, due to their structure and the fact that they are found in tomato seeds, it is likely that they are substantially nontoxic.

Preparation Procedures

Furostane Tetrasaccharide:

Furostane tetrasaccharide was isolated from tomato seeds (*Lycopersicum esculentum* Miller) as described by Sato and Sakamura (Agr. Biol. Chem., 37: 225–231, 1973). Furostane tetrasaccharide, the compound identified by Sato and Sakamura as the "bitter principle," has the chemical formula 5α-furostane3,β,22,26 triol-3-[0-β-D-glucopyronosyl (1→2)-β-D-glucopyronosyl (→4)-βD-galactoyranoside]

26-0-β-D-glucopyranoside, on the basis of spectral data and chemical and enzymatic degradation products. Essentially, dried tomato seeds were pulverized and subjected to multiple extractions with methanol. The methanol was subsequently removed by evaporation and the extracted chemicals were further extracted with ether. The residue was then dissolved in a minimum volume of methanol and loaded onto a silica gel column.

The silica gel column was made with silica gel of 100–200 mesh of average pore diameter 25 Angstroms (product number S 4133, Sigma Chemical Company St. Louis, MO). 80 g of silica gel were mixed with enough chloroform to make a slurry and loaded into a 47 cm×1.2 cm glass column. The extract residues, dissolved in methanol as described above, were then loaded onto the column and eluted with 30 ml chloroform. The column was then eluted with successive 10 ml volumes of a chloroform-methanol mixture, the first 10 ml containing 95% chloroform and 5% methanol; at each successive elution step the methanol content of the mixture was increased by 5%. Twenty four fractions of eluate were collected, each of 650 drops. Thereafter, fractions of 400 drops were collected. Fractions 30–55 were routinely tested for the presence of furostane tetrasaccharide by thin layer chromatography (TLC) and Staining with Ehrlich's reagent (p-dimethylaminobenzaldehyde; Sigma Chemical Co., St. Louis, MO) in 95% ethanol. Essentially, samples of eluate fractions were spotted onto precoated 5 cm×20 cm TLC plates precoated with silica gel 60, without fluorescent indicator (MCB Manufacturing Chemists, Inc., Cincinnati, OH). Chromatography was performed using a solvent comprising n-butanol-acetic acid-$H_2O$ (40:10:50). Furostane tetrasaccharide was identified by staining with Ehrlich's reagent; the compound stained red and had an $R_f=0.368$ using the described TLC technique.

Eluate fractions showing positive staining with Ehrlich's reagent (typically fractions 36–48) were pooled, evaporated to dryness and redissolved in 0.5 ml methanol. This material was then loaded onto an LH-20 column. The LH-20 column was prepared by mixing 10 g LH-20-100 sephadex (obtained from Sigma Chemical Co., St Louis, MO) with sufficient 50% (volume) methanol to form a slurry. The mixture was then de-gassed and packed into a 17 cm by 1.2 cm column. The sample was loaded onto the column and eluted with 50% (volume) methanol. One hundred drop fractions were collected and tested by TLC and staining with Ehrlich's reagent for the presence of furostane tetrasaccharide as described above. Fractions that tested positive were pooled, evaporated to dryness and lyophilized overnight to obtain off-white needle-like crystals. The yield of furostane tetrasaccharide produced by this method is typically approximately 1–2% of the total starting mass of tomato seeds.

Neotigogenyl Trisaccharide:

Neotigogenyl trisaccharide was prepared using the furostane tetrasaccharide as a starting material as described by Sato and Sakamura (1973). Essentially, 50 mg of furostane tetrasaccharide in 10 ml 0.1M phosphate buffer (pH 5.0) was incubated with 10 mg β-glucosidase (approximately 2,500 units/mg, catalog No. 100348, ICN Biochemicals, Inc., Irvine, CA) at 35° C. for 20 hours. The precipitates formed were collected by filtration, washed in water and then dried under vacuum.

An alternative method of directly producing neotigogenyl trisaccharide without the need for chromatography columns is as follows. Dried, crushed tomato seeds are extracted with methanol and, after removal of the seeds by filtration or centrifugation, the volume of the methanol is measured. A volume of water equivalent to 10% of the volume of methanol is then added to the methanol, together with activated charcoal, until all pigment color is lost. This preparation is then filtered and the filtrate evaporated to dryness. The residual solids are extracted with ether and the remaining solvent evaporated. The residue is then dissolved in 0.1M phosphate buffer (pH 5.0), β-glucosidase is added to approximately 20% weight and the mixture is incubated at 37° C. overnight. The resulting white precipitate is collected by filtration, washed three times with water and lyophilized. The neotigogenyl trisaccharide so produced has an $R_f=0.525$ by TLC performed as described above. Mass spectroscopy of the purified product yields a molecular weight of 902. The product is preferably stored at 4° C.

Furostene tetrasaccharide:

Furostene tetrasaccharide was prepared from furostane tetrasaccharide as follows: 180 mg of purified furostane tetrasaccharide, prepared as described above, were incubated at room temperature for two days with 2 ml pyridine and 8 ml of acetic anhydride. This mixture was then added to 20 ml of ice-cold water and the resultant white precipitate was collected by filtration using a 0.4 μM Millipore filter and dried by lyophilization. This precipitate is furostane tetrasaccharide peracetate. 200 mg of this compound were then refluxed at 120° C. for an hour with 4 ml acetic acid. The mixture was subsequently cooled and saturated sodium bicarbonate solution was added until no further bubbles were observed and the yellow pigment was lost. The mixture was then extracted with chloroform; the chloroform was evaporated to dryness and the resultant residue was dissolved in approximately 1 ml of methanol. A weighed amount of between 500–700 mg potassium hydroxide pellets was added to hydrolyze the acetate group. Thereafter, acetic acid was added in an equimolar amount to the potassium hydroxide to neutralize the potassium hydroxide. Finally, the furostene tetrasaccharide was purified by fractionation on a silica gel column as described above. Eluted fractions containing the furostene tetrasaccharide were identified by TLC chromatography as described above; furostene tetrasaccharide has an $R_f=0.473$.

Administration

This invention relates to certain glycosides which are potent inhibitors of cholesterol absorption and are therefore primarily useful for treatment of hypercholesterolemia. Since hypercholesterolemia is closely related to the development of generalized cardiovascular, cerebral vascular or peripheral vascular disorders, these compounds secondarily may prevent the development of atherosclerosis, particularly arteriosclerosis.

Cholesterol, which belongs to the body major plasma lipids, is highly soluble in fat but only slightly soluble in water. It is capable of forming esters with fatty acid and approximately 70% of the cholesterol present in plasma is in the form of cholesterol esters.

Cholesterol present in the body is either of endogenous or exogenous origin. Exogenous cholesterol is present in the diet and is absorbed slowly from the gastrointestinal tract into the intestinal lymph.

Endogenous cholesterol, in a rather large quantity, is formed in the cells of the body. Essentially, all the endogenous cholesterol that circulates in the lipoproteins of the plasma is formed by the liver, but all other cells of the body can and do form at least some cholesterol.

The major plasma lipids, including cholesterol, do not circulate free in the plasma, but are bound to proteins and transported as macromolecular complexes called lipoproteins.

The plasma lipoproteins can be separated into four major classes based, in part on their density (determined by the protein to lipid ratio):

1. chylomicrons;
2. very low density lipoproteins (VLDL);
3. low density lipoproteins (LDL); and
4. high density lipoprotein (HDL).

The lipoproteins can be successfully separated by ultracentrifugation or by electrophoresis. The pathological hyperlipoproteinemias, which will be treated by the method of this invention, are classified on the basis of the pattern of lipoprotein abnormalities.

Chylomicrons: The largest lipoprotein particles, the chylomicrons, contain the most lipids and are thus of the least density. They have high molecular weights ($10^9$ to $10^{10}$) and consist of a core of nonpolar lipids (mostly triglycerides) surrounded by a coat of protein, phospholipid, and free cholesterol. Chylomicrons are secreted into the intestinal lymphatics by the intestinal mucosa following the absorption of a lipid-containing meal, and their triglycerides are eventually stored in adipose tissue.

Very-Low-Density-Lipoproteins: The VLDLs are also triglyceride-rich. Their molecular weights are approximately $5\times10^6$. These molecules are secreted by the liver, and their triglyceride component is, in part, derived from dietary carbohydrates. Similar to the chylomicrons, VLDL triglycerides are mostly destined for storage in adipose tissue. On conventional electrophoresis, the VLDL migrate between the β- or low-density lipoproteins (LDL) and the α- or high-density lipoproteins (HDL). In this electrophoretic scheme the VLDL are thus termed pre-β-lipoproteins. Because of the high triglyceride content of the chylomicrons and the VLDL, an increase in their concentration is accompanied by elevation in the concentration of the plasma triglycerides.

The fraction of VLDL which is rich in cholesterol is called β-VLDL, which term is derived from the mobility of these lipoproteins. Like chemically altered LDL, β-VLDL are transported by scavenger cells into the blood vessel wall thus resulting in formation of atheromatous foam cells, the initiator of atheromatous plaques.

Low-Density-Lipoproteins: The low density lipoproteins have the electrophoretic mobility of β-globulins and are therefore known as β-lipoproteins. These lipoproteins contain the major portion of the total plasma cholesterol. When LDL are present in increased concentration, plasma cholesterol concentration is increased, while the triglyceride concentration is relatively normal.

High-Density Lipoproteins: The high density lipoproteins are considerably smaller particles. These lipoproteins contain about 50% of protein and have the electrophoretic mobility of α-globulins and are therefore terms α-lipoproteins. Of their lipids, phospholipids predominate. Plasma levels of HDL are inversely correlated with risk of atherosclerosis.

Depending on the plasma lipoprotein pattern, it is possible to classify patients with three types of hyperlipemia abnormalities: hypercholesterolemia, combined hyperlipemia and hypertriglyceridemia.

Hypercholesterolemia, combined hyperlipemia and hypertriglyceridemia occur commonly and involve two classes of lipoproteins (VLDL and LDL) for which there is a positive correlation between plasma concentration and the incidence of atherosclerosis.

1. Hypercholesterolemia is characterized by the presence of the LDL β-lipoproteins. It may be genetic, sporadic, or secondary to various defined causes such as hypothyroidism, nephrotic syndrome, myeloma, and excess dietary cholesterol. If the hypercholesterolemia is of genetic origin, clinical manifestations of the disorder are usually evident before the age of 30. Until that age the risk of vascular disease seems to be greatly increased. The studies have shown that about 50% of individuals suffering from the genetic (familial) hypercholesterolemia have myocardial infarction before the age of 50.

2. Combined hyperlipemia is characterized by the presence of both LDL β-lipoproteins and VLDL pre-β-lipoproteins. In combined hyperlipemia, both plasma cholesterol and triglyceride concentrations are elevated. In a study of 400 survivors of myocardial infarction, one third had hyperlipemia. Familial combined hyperlipemia, often associated with a β- and pre-β-lipoprotein pattern, is the most common genetic cause and accounts for 30% of the hyperlipemic group.

3. Hypertriglyceridemia is characterized by the VLDL pre-β-lipoproteins. Hypertriglyceridemia is frequently encountered and is likewise associated with an increased risk of atherosclerosis. Patients with hypertriglyceridemia exhibit sensitivity to carbohydrates; that is, to a diet high in carbohydrates. Such diet results in elevated plasma concentrations of VLDL, the triglyceride of which is in part synthesized by the liver from carbohydrates. In this disorder, glucose tolerance is commonly abnormal, and diabetes mellitus is frequently associated with such an excess of VLDL.

For reference to the above, see Guyton, *Medical Biology*, 5th Ed., pp. 926–927 (1976); *The Merck Index*, 13th Ed., pp. 381–383 (1977) and Goodman and Gilman, *The Pharmacological Basis of Therapeutics*, 5th Ed., pp. 744–747 (1975).

Inhibition of cholesterol absorption was studied in rats using the commonly recognized screening tests.

As described below, tests were performed to compare the effects of the compounds of the present invention on cholesterol absorption in rats compared to the known effect of tigogenin cellobioside. It was found that the compounds of the present invention produced lower cholesterol absorption and were thus more effective in removing the cholesterol from the plasma.

Administration of the compounds of the present invention, especially neotigogenin-trisaccharide, is preferably by oral administration. These compounds can be toxic if administered by other methods such as parental routes including intravenous, subcutaneous, intradermal, or intramuscular and other systemic routes of administration such as, for example, by suppositories.

The amount of neotigogenin trisaccharide administered will, of course, be dependent on the subject being treated, on the severity of the affliction, on the manner of administration and on the judgment of the prescribing physician. However, an effective dosage is in the range of 3 to 85 mg/kg/day, preferably 14 to 28 mg/kg/day. For an average 70 kg human, this would amount to 0.2 to 6 g/day, preferably 0.5 to 3 g/day, most preferably 1 to 2 g/day.

For oral administration, which is preferred, a pharmaceutical composition takes the form of solutions, suspensions, tablets, pills, capsules, powders, sustained release formulations and the like.

Pharmaceutical Composition

Depending on the intended mode of administration, the pharmaceutical compositions may be in the form of solid, semi-solid or liquid dosage forms, such as, for example, tablets, pills, capsules, powders, liquids suspensions, or the like, preferably in unit dosage forms suitable for single administration of precise dosages. The pharmaceutical compositions will include a conventional pharmaceutical carrier or excipient and, neotigogenin trisaccharide as an active ingredient. In addition, it may include other medicinal or pharmaceutical agents, carriers, adjuvants, etc.

A pharmaceutical composition may contain 0.1%–95% of neotigogenin trisaccharide, preferably 1%–70%. In any event, the composition or formulation to be administered will contain a quantity of neotigogenin-trisaccharide in an amount effective to alleviate the signs of the subject being treated, e.g. hypercholesterolemia or atherosclerosis.

For solid pharmaceutical compositions, conventional non-toxic solid carriers or excipients include, for example, pharmaceutical grades of mannitol, lactose, starch, magnesium stearate, sodium saccharin, talcum, cellulose, glucose, sucrose, magnesium carbonate, and the like.

Liquid pharmaceutically administerable compositions can be prepared by dissolving or dispersing, or otherwise preparing neotigogenin trisaccharide, and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see *Remington's Pharmaceutical Sciences*, Mack Publishing Company, Easton, Pa., 15th Edition (1975).

EXAMPLE I

Tomato Seeds Lower Cholesterol Absorption

Tests were performed on laboratory rats to determine the effect on cholesterol absorption when tomato seeds are incorporated into the diet. Tests were performed on laboratory animals according to the procedure outlined in M. R. Malinow, et al. "Effect of Alfalfa Saponins on Intestinal Cholesterol Absorption in Rats." *A.M. J. Clin. Nutr.*, 30, 2061–2067, 1977. The tests were performed in groups of six animals each. The results of these tests are summarized in Table I.

TABLE I

| Plant | Concentration in diet (%) | Number of rats | Choles. absorption* | % Controls | P |
|---|---|---|---|---|---|
| 0 | 0 | 6 | 69.2 ± 4.3 | | |
| Tomato Seeds | 40 | 6 | 36.1 ± 7.3 | 53 | <0.001 |

*% of injected dose; mean ± SD

As apparent from Table I, the incorporation of tomato seeds at 40% in the diet of rats reduces the absorption of cholesterol. This is contrary to the findings of Kintya et al. (Khin Pharm ZH, 15:55, 1981) who studied the effects of feeding tomato seed saponins on plasma cholesterol levels in rats made acutely hypercholesterolemic following the intraperitoneal injection of Tween-80.

Tomato seeds contain approximately 1.2% of a single saponin, which has sugar moieties on two opposite carbons of the aglycone structure, i.e. at C3 and C26, respectively. The chemical structure of this saponin, referred to herein as furostane tetrasaccharide, was established as 5α-furostane-3$_\beta$, 22, 26-triol-3-[0-β-D-glucopyranosyl (1→2)-β-D-galactopyranoside (1→4)-β-D-galactopyranoside] 26-0-β-D-glucopyranoside by Sato and Sakamura, *Agric. Biol. Chem.*, 37, 225, 1973. The aglycone moiety in this compound is neotigogenin.

EXAMPLE II

Effect of Purified Neotigogenyl Derivatives on Intestinal Absorption of Cholesterol in Rats The effects on cholesterol absorption of the furostane tetrasaccharide saponin present in tomato seeds (*Lycosperiscum esculentum* Miller) and two derived glycosides (Sato and Sakamura, 1973), were tested in rats with a modification of the method of Kelley and Tsai (Kelley and Tsai, "Effect of Pectin, Gum Arabic and Agar on Cholesterol Absorption, Synthesis and Turnover in Rats," *J. Nutr.*, 108:630–639, 1978) as adapted by Harwood et al. (Harwood et al., "Pharmacologic Consequences of Cholesterol Absorption Inhibition: Alteration in Cholesterol Metabolism and Reduction in Plasma Cholesterol Concentration Induced by the Synthetic Saponin β-tigogenin Cellobioside (CP-88818; tiqueside)," *J. Lipid Res.*, 34:377–395, 1993)

Male white rats weighing around 200 g were chow fed during an adjustment period. They were then weighed and assigned randomly to 5 groups of 6 rats each. Subsequently, they were fasted overnight and offered 5% dextrose/saline ad libitum. On the day of the experiment, the animals were anesthetized with ether and a 5 French cannula (Baxter, Deerfield, IL) was introduced into the stomach. The following were injected intragastrically:

1. 2 ml of solution A (controls) or solution A containing 20.8 μmoles of any one of the 4 glycosides listed in I–IV below:

I. Tigogenyl cellobioside (U.S. Pat. Nos. 4,602,003; 4,602,005)

II. Furostane tetrasaccharide

III. Neotigogenyl trisaccharide

IV. Furostene tetrasaccharide 2. 1.5 ml of solution B containing about 1.1 μCi of $^{14}$C-4-cholesterol (specific activity 52 mCi/mmol; Amersham, Arlington, IL) and about 2 mg of cholesterol (5.2 μmoles)

3. 1.5 ml liquid diet (Ross Laboratories, Columbus, OH) diluted 50% in water 4. 0.5 ml of 5% dextrose saline Preparation of solutions: Solution A comprised 75 ml 10% ethanol, 225 mg Tween 80 and 187.5 mg methylcellulose. Solution B comprised 50 ml of 90% ethanol, 300 mg of cholic acid and 66.67 mg cholesterol. Approximately 50 μCi of 14C-4-cholesterol were placed in a 50 ml tube and approximately 40 ml of solution B were added. Solutions A and B were sonicated briefly and stirred continuously until used.

Following the injections, the rats were offered 5% dextrose/saline ad libitum.

Twenty-four hours after injection, the rats were anesthetized with ether, blood was obtained through cardiac puncture, introduced into tubes containing EDTA, centrifuged and the plasma was separated and frozen until analyzed. The liver was excised, blotted and weighed, cooled and then frozen until analyzed. Radioactivity was determined in an aliquot of the $^{14}$C-4-cholesterol- containing mixture and in plasma as follows: 100 μl of the $^{14}$C-4-cholesterol-containing mixture, or 200 μl of plasma were introduced into 5 ml polypropylene scintillation vials (USA/Scientific Plastics, Ocala, FL.). Thereafter, 200 μl of $H_2O_2$ and 5 ml of scintillation fluid (ScintiVerse, Fisher Scientific, Pittsburgh, Pa.) were added. Cholesterol absorbed and taken into the liver was determined by weighing a thawed slice of explanted liver (of approximately 100 mg), placing the slice in a 20 ml glass scintillation vial (VWR Scientific, Seattle, WA.), and adding 1 ml of Solvable (NEN Research Products, Boston, Mass.) and 12 ml scintillation fluid. All samples were counted in a Packard Scintillation Spectrophotometer using an automatic external standard. All results were obtained as DPM.

The cholesterol absorbed was calculated assuming a plasma volume of 4% of body weight (Altman and Dittmer, *Biology Data Book*. Second edition, Vol. III, 1974, pp. 1847. Federation of American Societies for Experimental Biology, 1974). The plasma radioactivity was added to that calculated for the whole liver. All injections were standardized to $2.4 \times 10^6$ DPM; results indicated as percent absorption of the control rats are shown in Table II.

TABLE II

| Group | Number of Rats | Body Weight (g) | Liver Weight (g) | Cholesterol Absorption |
|---|---|---|---|---|
| Controls | 6 | 237 ± 9 (SD) | 9.03 ± 0.51 | 1.0[a,b]*** |
| I* | 6 | 233 ± 5 | 8.35 ± 0.98 | 0.42[a,c] |
| II* | 5** | 230 ± 14 | 8.66 ± 1.10 | 0.64 |
| III* | 6 | 230 ± 7 | 8.20 ± 0.80 | 0.16[b,c] |
| IV* | 5** | 225 ± 2 | 8.18 ± 0.89 | 0.64 |

*For chemical structure of glycosides, see above.
**One rat in each group killed accidentally during the injections.
***Data sharing similar superscripts are significantly different. Student's "t" test: a, $p < 0.05$; b, c, $p < 0.01$.

The above results indicated that the tomato seed glycoside furostane tetrasaccharide and derivatives of this glycosides reduce the intestinal absorption of cholesterol. These compounds contain a neotigogenin aglycone moiety. The 25-β neotigogenin aglycone has a chemical structure that differs significantly from other aglycones, such as 25 α-tigogenin, found in glycosides that interfere with cholesterol absorption. Furthermore, in preferred embodiments such as neotigogenin trisaccharide, the glycosides of the present invention containing the neotigogenin glycone are approximately 2–3 times more effective than glycosides containing the tigogenin aglycone such as tigogenyl cellobioside. It is proposed that this enhanced efficacy is attributable to the spacial configuration of the 25 $CH_3$ which is in the axial (L or β) configuration in neotigogenin and in the equatorial (D or α) configuration in tigogenin.

In addition to the enhanced efficacy of neotigogenin-based glycosides, the compounds of the present invention offer a number of other advantages over the tigogenin-based glycosides. The starting material for producing neotigogenin-based glycosides is tomato seeds; tomato seeds are much more readily available in the United States and other countries than the plants from which tigogenin is obtained. Additionally, large amounts of tomato seeds are thrown away every year as waste products in the tomato-processing industry; such presently wasted seeds will provide a readily available and economical source of the neotigogenin-based glycosides. Furthermore, the neotigogenin-based glycosides are present in tomato seeds in a glycosylated form that can easily be converted into more active forms such as neotigogenin trisaccharide. In contrast, tigogenin isolated from *Agave sisalana* is not glycosylated and must be converted into a glycosylated form to produce active compounds such as tigogenin cellobioside. The required glycosylation reactions are complex and require the use of large amounts of environmentally hazardous organic solvents as well as heavy metal catalysts. Finally, because the neotigogenyl-based glycosides are found in tomato seeds, a common food, these compounds are likely to meet with ready consumer acceptance and are not anticipated to have any toxicity to mammals.

Alternative Embodiments

The glycoside compounds of the present invention comprise a sugar moiety linked to a neotigogenin aglycone, such as furostene, furostane or neotigogenin itself. The compounds of the present invention are shown as possessing a sugar moiety comprising β-D-glucopyranosyl (1→2)-β-D-glucopyranosyl (1→4)-β-D-galactopyranoside linked to the C3 carbon of the aglycone, as shown below:

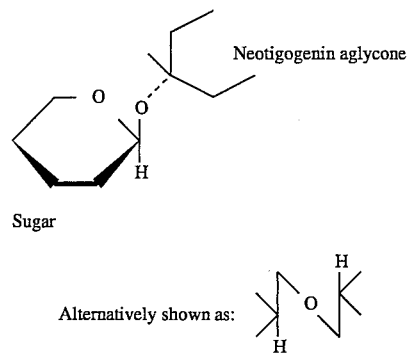

The naturally occurring enantiomer of these compounds with respect to the glycosidic bond between the carbohydrate-containing molecule and the aglycone (i.e the C3-sugar linkage) is almost exclusively the β enantiomer shown in the formula above (Heftmann and Mosettig, 1960). However, it will be appreciated by one skilled in the art that the glycosidic bonds between the carbohydrate-containing molecule and the aglycone could alternatively be an α glycosidic bond:

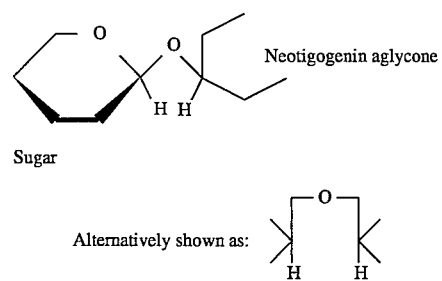

For compounds which are to bind cholesterol, it is anticipated that a β glycosidic bond will be preferred in most instances since compounds having a β glycosidic bond are less likely to be hydrolyzed in the intestine of the subject animal. According to the present invention, neotigogenin trisaccharide that contains a β-linkage between the neotigogenin aglycone and the trisaccharide moiety is referred to as β-neotigogenin trisaccharide. Where no α or β designation is set forth, either form of the molecule, or a mixture of both forms, is intended.

One skilled in the art will also appreciate that derivatives of the trisaccharide-containing molecules disclosed may be obtained by replacing the trisaccharide moiety with other carbohydrate moieties. Variations of the disclosed molecules that have different carbohydrate moieties can be readily produced by known chemical reactions. Thus, for example, the carbohydrate moiety disclosed could be replaced with the monosaccharide α-D-(+)-glucose of the formula:

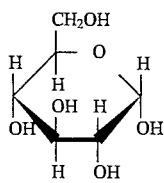

or β-D(+)-glucose of the formula:

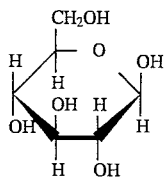

Other suitable carbohydrates include other monosaccharides such as galactose, disaccharides such as glucose-galactose or, as disclosed in U.S. Pat. No. 4,602,003, (+)-cellobiose (β-anomer) otherwise known as 4-0-(β-D-glucopyranosyl-D-glucopyranose):

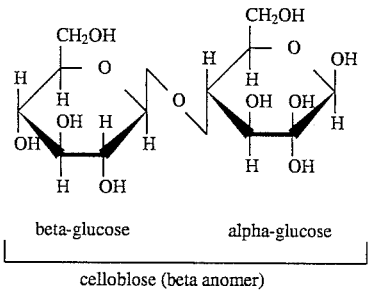

celloblose (beta anomer)

It is anticipated that larger carbohydrate moieties can also be substituted for the disclosed carbohydrate moieties. The suitability of particular carbohydrate substitutions for use in cholesterol absorption can be readily ascertained by the methods disclosed herein.

In other embodiments of the present invention, esters of neotigogenin can be prepared by reacting an anhydride with the neotigogenin or a derivative of neotigogenin. Any of numerous organic and hydride substances could be used in such molecules, although not all such molecules would be effective or be sufficiently nontoxic for general use. Esters may be formed from the following anhydrides which react with the hydroxyl group of the neotigogenin:

| Anhydrides Useful in the Synthesis of Neotigogenin Esters | |
|---|---|
| phtalyl-DL-glutamic | cis-1,2-cyclobutanedicarboxylic |
| 1-octenyl-succinic | citraronic |
| glutaric | 3-nitrophtalic |
| nonenylsuccinic | methylsuccinic |
| trans-1,2-cyclohexane dicarboxylic | 3-methylglutaric |
| cix-1.2-cyclohexanedicarboxylic | 2.3-dimethyl maleic |
| 3.3-dimethyl glutaric | 1.2.3.4-cyclobutane tetracarboxylic |
| trans-1.2-cyclohexanedi- carboxylic | diphenyl |
| 2-dodecen-1-ylsuccinic | maleic |
| dichloromaleic | |

For example, maleic esters are synthesized by combining maleic anhydride and neotigogenin in chloroform at 50° for a period of four days.

Tests to determine the efficacy of esters of neotigogenin in reducing cholesterol absorption are performed on laboratory animals according to the procedure outlined in "Effect of Alfalfa Saponins on Intestinal Cholesterol Absorption in Rats." *Am. J. Clin. Nutr.*, 30, Dec. 1977, pps. 2061–2067.

Having given the examples of particular embodiments of my invention, it will be apparent to those skilled in the art that changes and modifications may be made without departing from my invention in its broader aspects. I therefore intend the appended claims to cover all such changes and modifications as fall within the true spirit and scope of my invention.

I claim:

1. A method of reducing cholesterol absorption in a digestive system of a mammal, comprising administering to the mammal a therapeutically effective amount of the compound neotigogenin trisaccharide.

2. A method of reducing cholesterol absorption in a digestive system of a mammal, comprising administering to the mammal a therapeutically effective amount of the compound β-neotigogenin trisaccharide.

3. A pharmaceutical composition useful for reducing cholesterol absorption in the digestive system of a mammal, the composition comprising a therapeutically effective amount of neotigogenin trisaccharide in admixture with a pharmaceutically acceptable excipient.

4. A pharmaceutical composition useful for reducing cholesterol absorption in the digestive system of a mammal, the composition comprising a therapeutically effective amount of β-neotigogenin trisaccharide in admixture with a pharmaceutically acceptable excipient.

\* \* \* \* \*